United States Patent [19]

Sergienko

[11] Patent Number: 4,642,115
[45] Date of Patent: Feb. 10, 1987

[54] ARTIFICIAL EYE LENS

[75] Inventor: Nikolai M. Sergienko, Kiev, U.S.S.R.

[73] Assignee: Kievsky Nauchno-Issledovatelsky Institut Klinicheskoi I Experimentalnoi Khirurgii, Kiev, U.S.S.R.

[21] Appl. No.: 848,722

[22] PCT Filed: Aug. 6, 1984

[86] PCT No.: PCT/SU84/00047
§ 371 Date: Apr. 4, 1986
§ 102(e) Date: Apr. 4, 1986

[87] PCT Pub. No.: WO86/01096
PCT Pub. Date: Feb. 27, 1986

[51] Int. Cl.⁴ .............................................. A61F 2/16
[52] U.S. Cl. ....................................................... 623/6
[58] Field of Search ............................................ 623/6

[56] References Cited

U.S. PATENT DOCUMENTS

| | | | |
|---|---|---|---|
| 3,673,616 | 7/1972 | Fedorov | 623/6 |
| 3,922,728 | 12/1975 | Krasnov | 623/6 |
| 4,242,760 | 1/1981 | Rainin | 623/6 |
| 4,316,292 | 2/1982 | Alexeev | 623/6 |
| 4,366,582 | 1/1983 | Faulkner | 623/6 |
| 4,437,194 | 3/1984 | Hahs | 623/6 |
| 4,536,895 | 8/1985 | Bittner | 623/6 |
| 4,579,557 | 4/1986 | Fedorov et al. | 623/6 |

FOREIGN PATENT DOCUMENTS

| | | | |
|---|---|---|---|
| 545352 | 2/1977 | U.S.S.R. | 623/6 |
| 858819 | 8/1981 | U.S.S.R. | 623/6 |

Primary Examiner—Ronald L. Frinks
Attorney, Agent, or Firm—Lilling & Greenspan

[57] ABSTRACT

An artificial eye lens (1) comprises an optical lens (2) and three supporting elements one of which is shaped as a loop (3), while the two other elements are made as V-shaped legs (4). The loop (3) and the legs (4) are situated on the diametrically opposite sides of the lens (2). Each of the legs (4) is secured with one of its sides (5) on the anterior surface of the lens, is inclined towards the posterior lens surface so that the other side (7) of the leg is situated in the lens principal plane. The legs diverge along the lens (2) lateral surface, and the ends of the leg sides (5 and 7) face each other.

2 Claims, 3 Drawing Figures

ARTIFICIAL EYE LENS

This application is based on International Application PCT/SU 84/00047 filed Aug. 16, 1984.

TECHNICAL FIELD

The present invention relates generally to medicine and more specifically to ophthalmology, having particular reference to an artificial eye lens.

PRIOR ART

It is common knowledge that surgical treatment of various eye diseases necessitates very frequently the removal of the crystalline lens (lensectomy) followed by its substitution with an artificial (intraocular) lens. As a rule, the majority of such artificial lenses need further suturing of the supporting elements to the iris, which is in fact a rather complicated surgical intervention, especially when the lens is to be fixed to the inferior portion of the iris. This operation is fraught with possible dislocation of the lens when the pupil is being dilated, which may be the case if the lens is introduced through a puncture in the iris as it is known, e.g., from USSR Inventor's Certificate No. 545,352, wherein an artificial lens provides for the presence of a lens and supporting legs outside the pupillary area, and the lens has at least one loop-shaped leg to pass a suture attaching the lens to the iris.

With a view to attaining a simplified artificial lens implantation technique and its more reliable fixing, another artificial eye lens has been devised, described in USSR Inventor's Certificate No. 858,819. In such an artificial lens the top loop-shaped leg is in effect composed of two lugs arranged oppositely each other in a horizontal plane of the lens in its top portion, and the plane of said loop-shaped leg is offered at an angle of from 5 to 8 degrees with the plane of the lens so as to establish springiness. A bottom supporting leg is also provided.

A disadvantage inherent in the aforesaid known artificial lens resides in the fact that it involves the formation of a large incision (up to 4 mm long) in the top portion of the iris followed by application of a Supramide (R) suture, which prolongs substantially the operative time and offers additional technical difficulties during the lens implantation. Moreover, a possibility cannot be ruled out for the pupil deformation and enlargement of the incision as a result of the suture cutting through thinned distrophically changed structures resulted from a prolonged compression of the iridal tissues. This in turn may lead not only to dislodging but also to off-centring of the artificial eye lens. In addition, such an artificial eye lens may rather frequently be the cause of an inflammatory reaction of the eye due to forceful interaction of the lens supporting elements with the eye tissues rich in blood vessels and nerves.

ESSENCE OF THE INVENTION

It is an essential and primary object of the present invention to provide the supporting elements of an artificial eye lens made in such a manner as to ensure simple and convenient implantation of the artificial lens, render the operative techniques simpler, attain more reliable attachment of the eye lens and make the operation less traumatic.

The aforesaid object is accomplished due to the fact that in an artificial eye lens, comprising a lens proper and three supporting elements, one of which is formed as a loop and the two other are arranged at the same side of the lens oppositely to said loop-shaped element, according to the invention, each of the two elements situated on the same side of the lens is shaped as a V-shaped leg fastened on the lens anterior surface with one of the ends of its one side, and due to the fact that the sides of the V-shaped legs diverge along the lateral lens surface and are inclined towards the posterior surface of the lens in such a manner that the other sides of said legs are situated in the lens principal plane and faces each other with the vacant ends of the legs.

An advantageous feature of such an artificial eye lens consists in that large incisions in the iris are no longer necessary due to the aforesaid orienting of the two V-legs made fast on the anterior lens surface, since no necessity arises for passing the V-shaped legs behind the iris no matter whether the lens is set in the posterior or in the anterior eye chamber. This in turn makes it possible to simplify the lens implantation techniques and to render the surgery less traumatic. In addition, the construction proposed herein provides for pinpoint accuracy of the lens centring in the eye and practically rules out its decentration.

It is expedient that an elbow be provided in the side of each V-shaped legs fastened on the lens anterior surface to facilitate fastening of this side on the lens.

Such a constructional arrangement of an artificial eye lens adds much to facility of surgeon's manipulation when positioning the lens in the posterior eye chamber of the patient.

PREFERRED EMBODIMENTS OF THE INVENTION

Figure 1:
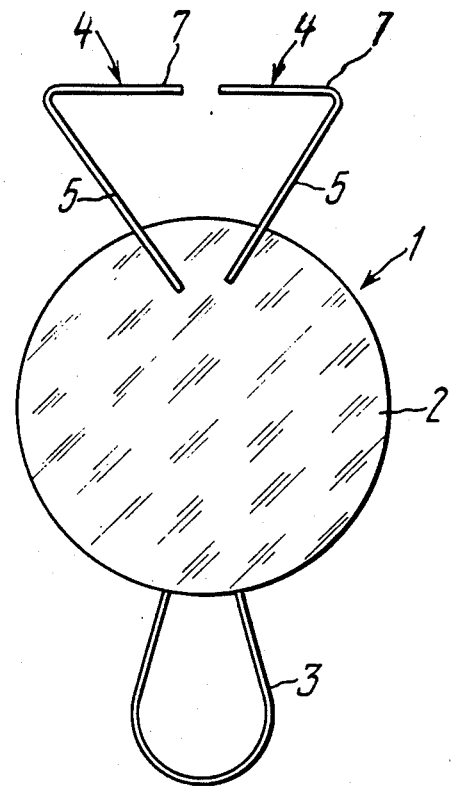
FIG. 1 is a front view of an artificial eye lens, according to the invention.

Now referring to FIG. 1, Ref. No. 1 denotes an artificial eye lens as a whole, which comprises a lens 2 proper and three supporting elements one of which is shaped as a loop 3, while the two other are shaped as legs 4 and are situated on the diametrically opposite side of the lens 2.

Figure 2:
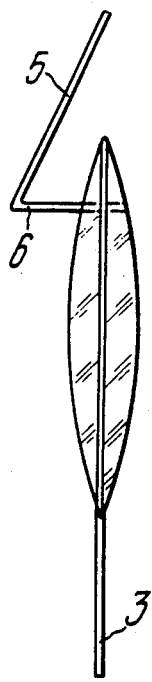
FIG. 2 is a side view of an artificial eye lens as shown in FIG. 1 intended for implantation in the posterior eye chamber.
Figure 3:
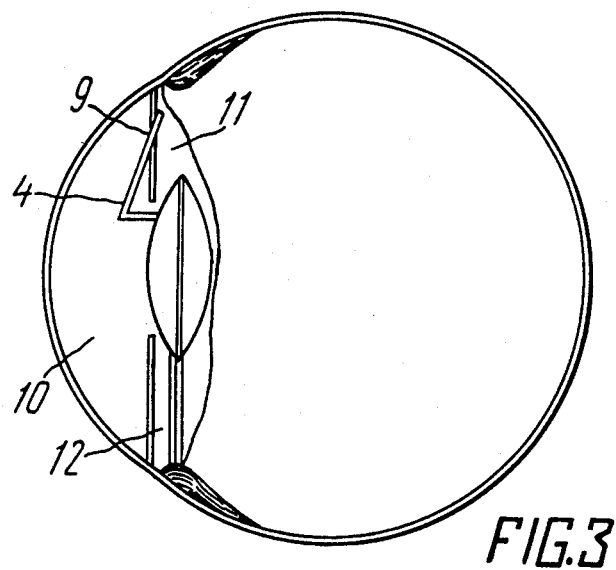
FIG. 3 is a side view of an artificial eye lens designed for implantation in the anterior eye chamber.

Used as the lens 2 may be an optical lens of any heretofore-known construction suitable for the purpose, e.g., a biconvex lens as can be best seen from FIGS. 2 and 3.

The supporting element shaped as the loop 3 is made of a highly elastic material, e.g., Supramide (proprietary name), and is fixed with its both ends in the lens.

As it has hereinbefore stated and can be seen from FIG. 1, two V-shaped legs are provided on the side of the lens 2 diametrically opposite to the loop 3 and are made of an elastic material such as Supramide. It is said two V-shaped legs that provide for an advantageous feature of the present invention. As it can be seen from FIG. 1 V-shaped legs 4 are secured with one of its sides 5 on the anterior surface of the lens 2 so as to diverge along the lateral surface of the lens 2. The legs 4 may be fixed to the lens with one side 5 either directly as shown in FIG. 3 or through the agency of an elbow 6 as seen in FIG. 2. In both cases the sides 5 are inclined towards the posterior surface of the lens 2 so that another side 7 of the V-shaped leg is arranged in the principal plane of the lens, which can be well seen in FIG. 2. With such orientation of the sides of the legs 4 the vacant ends of the sides 7 face each other substantially square with the optical axis, a gap being left therebetween.

It also deserves attention that the artificial lens shown in FIG. 2 and designed for implantation in the anterior eye chamber, features an elbow in the loop 3, whereby additional fixation of the lens in the eye is attained.

Now let us consider briefly the implantation techniques of the artificial eye lens as shown in FIG. 2, into the posterior eye chamber.

The intervention begins with a limbal incision made within the segment of 10 and 2 o'clock. Using a special instrument the place for iridotomy is marked out, whereupon punctiform iridotomies 9 are made along the 11 and 1 o'clock meridians (FIG. 3). Then air is admitted to pass into the anterioir eye chamber. Using special forceps the artificial eye lens is caught by its legs 4 close to the point of its holding to the lens 2. The loop 3 and the lens 2 are introduced through the limbal incision into the anterior eye chamber 10, then through the pupil into the posterior eye chamber 11. The loop 3 is interposed between the leaves of the crystalline capsule 12 along the 6 o'clock meridian and is fixed with a duplicate holder 12. Next the forceps holding the artificial eye lens, is brought out of the ocular cavity. The legs 4 are left in the anterior eye chamber, while their sides 7 are brought, by means of forceps, into punctiform iridotomies made along the 11 and 1 o'clock meridian beforehand. Thereupon air and physiological saline are admitted into the anterior eye chamber. Next loop silk sutures are applied to the limbal incision, while the conjunctival wound is stitched up with a continuous suture.

Some exemplary case histories are described hereinbelow.

Female patient S., aged 34 was admitted to the ophthalmological department on Dec. 12, 1983 with the diagnosis of complicated cataract of both eyes.

On admission:
 OD—correct light projection
 OS—0.1 n/c

On Dec. 13, 1984 a surgical intervention was performed: extracapsular cataract extraction followed by implantation of a posterior-chamber artificial eye lens 22 OD on the right eye. The surgery and post-operative period uneventful.

At dismissal:
 OD—0.8/1.0 c+1.0 yl, axis 90°
 OS—0.1 not corrected.

Now let us consider briefly the implantation techniques of the artificial eye lens as seen in FIG. 3, according to the invention, into the anterior eye chamber.

A limbal incision is performed within the segment of 10 and 2 o'clock. Using a special instrument the place for iridotomies is marked out, whereupon punctiform iridotomies are made along the 11 and 1 o'clock meridians. Air is admitted to pass into the anterior eye chamber. Using forceps the artificial eye lens is caught by its legs 4. The loop 3' is introduced through the limited incision into the anterior eye chamber 10, then through the pupil into the posterior eye chamber. The forceps holding the artifical eye lens is brought out of the ocular cavity. Now the lens 2 of the artificial eye lens is located in the anterior eye chamber. The legs 4 are left in the anterior eye chamber and their sides 7 are brought, by means of forceps, into punctiform iridotomies made along the 11 and 1 o'clock meridians beforehand. Then air and physiological saline are admitted into the anterior eye chamber. Loop silk sutures are applied to the limbal incision, while the conjunctival wound is stitched up with a continuous suture.

Male petient G., aged 22 was admitted to the ophthalmological department on Jan. 17, 1984 with the diagnosis of aphakia of the left eye.

On admission: OD—1.0; OS—1.0 c+11.0 D

On Jan. 18, 1984 implantation of the anterior-chamber artificial eye lens 17 OD was carried out. The surgery and post-operative period uneventful.

At dismissal: OD—1.0, OS—1.0.

INDUSTRIAL APPLICABILITY

The herein-proposed artifical eye lens is applicable for correction of aphakia involved in surgery of senile or traumatic cataracts.

What is claimed is:

1. An artificial eye lens, comprising a lens proper and three supporting elements, one of which is shaped as a loop (3), while the two other elements are arranged on the same side of the lens (2) diametrically opposite to the loop-shaped element, characterized in that each of the elements located on the same side of the lens (2) is made as V-shaped legs (4) made fast on the anterior surface of the lens (2), with the end of their one side (5), and in that said sides (5) of the V-shaped legs diverge along the lateral surface of the lens (2) and are inclined towards the posterior lens surface so that the other sides (7) of said legs are situated in the lens principal plane and face each other with the vacant ends of the legs.

2. An artificial eye lens as claimed in claim 1, characterized in that the side of each leg fastened on the anterior surface of the lens has an elbow (6) for said side (5) to be secured on the lens.

* * * * *